United States Patent [19]

Xanthopoulos

[11] Patent Number: 4,537,561
[45] Date of Patent: Aug. 27, 1985

[54] PERISTALTIC INFUSION PUMP AND DISPOSABLE CASSETTE FOR USE THEREWITH

[75] Inventor: Piritheos E. Xanthopoulos, San Jose, Calif.

[73] Assignee: Medical Technology, Ltd., Fresno, Calif.

[21] Appl. No.: 469,421

[22] Filed: Feb. 24, 1983

[51] Int. Cl.³ .................. F04B 43/12; F04B 21/00
[52] U.S. Cl. .................................. 417/63; 417/477; 128/DIG. 12
[58] Field of Search ............. 604/153; 128/DIG. 12; 417/474–478; 418/45

[56] References Cited

U.S. PATENT DOCUMENTS

| | | | |
|---|---|---|---|
| 2,483,924 | 10/1949 | Moulinier | 417/477 X |
| 3,658,445 | 4/1972 | Pulman et al. | 417/474 |
| 3,690,318 | 9/1972 | Gorsuch | 128/DIG. 12 X |
| 3,737,251 | 6/1973 | Berman et al. | 417/475 X |
| 3,829,249 | 8/1974 | Pursley | 417/477 X |
| 4,187,057 | 2/1980 | Xanthopoulos | 417/63 |
| 4,218,197 | 8/1980 | Meyer et al. | 417/477 X |
| 4,229,299 | 10/1980 | Savitz et al. | 417/477 X |
| 4,256,437 | 3/1981 | Brown | 417/45 |
| 4,303,376 | 12/1981 | Siekmann | 417/474 X |

FOREIGN PATENT DOCUMENTS

| | | | |
|---|---|---|---|
| 1441391 | 6/1976 | United Kingdom | 417/477 |
| 2075128 | 11/1981 | United Kingdom | 417/477 |

*Primary Examiner*—Carlton R. Croyle
*Assistant Examiner*—T. Olds
*Attorney, Agent, or Firm*—Thomas E. Schatzel

[57] ABSTRACT

An improved peristaltic infusion pump and disposable cassette for use therewith. The cassette includes a hollow conduit arrangement with a section of elastic tubing and adapted to pass intravenous fluids therethrough. The conduit is fixedly mounted in a rigid cassette wherein an intermediate section of the elastic tubing is free to move in a direction perpendicular to the base of the cassette. The infusion pump includes a pump cassette housing designed to properly align and support the cassette and encloses a pump rotor assembly designed to interface with the elastic tube of the cassette so as to generate a peristaltic force in the hollow conduit arrangement.

5 Claims, 17 Drawing Figures

Fig_6

Fig_8

Fig_7

Fig_9

Fig_10

Fig_11

Fig_12

Fig_14

Fig_13

PERISTALTIC INFUSION PUMP AND DISPOSABLE CASSETTE FOR USE THEREWITH

BACKGROUND OF THE INVENTION

1. Field of the Invention

The present invention relates generally to an infusion pump for use in medical applications and more particularly to an improved pump system utilizing a specially designed peristaltic infusion pump and disposable cassette.

2. Description of Prior Art

Presently there are two methods to medically administer intravenous "IV" fluids. Either a pure gravity feed or an infusion pump system can be utilized to dispense IV fluids to a patient. The gravity system does not require external energy. However, it is limited as to the amount of fluids it can dispense within a specified time. The infusion pump system is capable of administering greater quantities of IV fluids to a patient in a shorter period of time. However, it requires an external power source to function.

The present invention relates more to the infusion pump method of IV fluid administration, but, under certain circumstances can function as a gravity feed system. To accomplish this dual function, the infusion pump uses a disposable cassette which can be used with an infusion pump or detached from the pump and positioned above the patient allowing gravitational pressure to dispense the IV fluid. When the disposable cassette is engaged with the pump, a rotary device rhythmically compresses and releases a portion of elastic tubing to produce a peristaltic pressure thereby forcing the IV fluid in the tube to flow toward the patient.

As with other critical life support equipment, the pump must be reliable, very accurate and easy to operate during emergency situations. Also, the pump must be inexpensive to manufacture and operate to ensure that the spiraling cost of health services today are controlled in the future.

The use of peristaltic pump-disposable cassette system is known in the prior art. Such a system is described in U.S. Pat. No. 4,187,057 which discloses the construction of a disposable cassette and peristaltic pump. In that patent the disposable cassette utilizes a section of elastic tubing to interface with a pump rotor to create the peristaltic pressure. The peristaltic pump utilizes a three-step sequence to load or unload the disposable cassette. While U.S. Pat. No. 4,187,057 is capable of performing the functions of a peristaltic pump it contains certain serious disadvantages.

One disadvantage to the more conventional pump design relates to the cost and expenses associated with the manufacture of the disposable cassette. The prior art specifically dictates that the disposable cassette be manufactured in two separate pieces, with precision internal passages and a precise 180° arcuate surface. These requirements necessitate the use of costly special tooling to fabricate the cassette halves and the use of expensive labor to assemble the cassette pieces.

Another disadvantage of the structure of the aforementioned patent concerns its use of a section of translucent tubing to facilitate the monitoring of the IV fluid's contents. Use of such tubing is expensive, as such tubing must be of the highest quality and translucent consistency for the IV monitor to function.

A third disadvantage with the prior patent design is a persistant unresolved problem with all peristaltic infusion pumps. Specifically the migration or creeping of elastic tubing around the head of the pump rotor assembly. This results in inaccurate pumping pressures and IV fluid flow rates. In the known prior art peristaltic pumping force is generated by rapid and repeated squeezing of an elastic tube, filled with an IV fluid, against a smooth backing surface by means of a pump rotor assembly. This process of generating peristaltic force causes a portion of the elastic tubing to migrate or creep around the pump rotor assembly due to the unequal coefficients of friction exerted upon the elastic tube. When the pump rotor assembly squeezes the tube, it propels the upper portion of the tube in one direction while the back or lower section of the tube, not exposed to the pump rotor assembly, is being held back by the backing surface. This results in a greater portion of the upper part of the tube being forced along in the direction of the pump rotor causing the tube to grow increasingly narrow on one side of the pump rotor assembly while growing increasingly thick on the other. This effect continues until the elastic limit of the tube is reached and the migrated tubing snaps back into its initial place on the other side of the pump rotor assembly. During the period of time just prior to the tube snapping back into place, the diameter of a portion of the tube is greatly reduced limiting the quantity of IV fluid which can pass through the tube. At the instant the tube snaps back into its original position, the pressure in the IV tube drops dramatically. This drop in pressure is due in part to the fact that the constricted portion of tube is instantly increased to its initial diameter. As expected, these changes in the diameter and pressure of the tube cause pumping inaccuracies. The affects manifest themselves in fluctuating IV pressure and an inability to precisely measure the quantity of IV fluids being administered by the pump. U.S. Pat. No. 4,187,057 attempts to rectify these problems by fixedly supporting the two ends of the elastic tube within the cassette and by utilizing a 180° arcuate tube backing surface. While such design reduces the unwanted "creep" affects, it does not alleviate the problem.

Another inherent problem associated with the "creep" affects previously discussed focuses on the unintended distortions perpetrated on the elastic tube when it "creeps" around the pump rotor assembly and snaps back. Under these circumstances the operational life of the elastic tube is greatly reduced compared to that if no such abuse were inflicted on the tube. The decreased operational life of a plastic tube greatly impacts the patients' safety if the cassette is not replaced frequently and with frequent replacement of the cassette esculates costs.

Another problem associated with the use of peristaltic pumps concerns the lengthy procedure required to properly load or unload a disposable cassette from a pump. In emergency situations, when the cassette must be loaded or unloaded quickly, previous machines could not be relied upon to provide a smooth efficient method for loading or unloading the cassette. Specifically, U.S. Pat. No. 4,187,057 describes a three-step loading/unloading procedure unsuitable for use under hurried conditions. The three-step procedure requires: (1) that a cassette supporting structure be lowered; (2) that the cassette be inserted into the lowered cassette supporting structure; and (3) that a cammed shaft be rotated to raise the cassette into contact with the pump rotor assembly. As stated, this complex and time consuming operation could not satisfactorily be performed under emergency situations.

In conjunction with other problems, the prior art failed to produce an easy economical way to determine if the cassette was properly in an operational position. In U.S. Pat. No. 4,187,057 the solution to this problem required a visual check that the cam shaft had been properly rotated and that the cassette was in position. The solution to the problem was ineffectual. Inexperienced pump operators could not visually recognize when the proper shaft had been rotated or if the cassette were properly engaged. The results of a disengaged cassette thought to be in an operating position can be quite serious, due to the fact that when a cassette is not in its operative position IV fluid will not be pumped into the patient as prescribed.

Another problem associated with the use of a support or backing surface for the elastic tube manifests itself in the expense related to the use of only high quality elastic tubing of specific inner and outer diameter. Such expensive tubing is required because if a less expensive tubing, with inconsistent diameters, is utilized undesired pressure and flow inaccuracies result. If a tubes' outer diameter is too large, it will totally occulate under compression preventing fluid flow and causing premature tube failure. If the tubes' outer diameter is too small or narrow, the pump rotor assembly will not squeeze the tube with enough force to propagate the required peristaltic action. None of the known prior art has addressed this problem and all rely on the use of very expensive tubing in an attempt to diminish the probability of tube diameter affecting pump performance.

Another problem, not resolved in the prior art, concerns the leakage of corrosive solvents into internal pump mechanisms. This problem results in improper pump operations and, could upon occasion, totally disable the pump. The consequences of such a malfunction to the patient are serious. There are two major causes for such leakage; a leak in the IV tube/disposable cassette could deposit corrosive solutions in the pump's internal mechanisms; or a battery, internal to the pump could rupture inflicting similar pump damage.

Additionally, the prior art does not address the problem associated with the external interruption of the pump rotor assembly. Specifically, U.S. Pat. No. 4,187,057 teaches the use of an exposed pump motor shaft. As pump motors are designed to deenergize when a specified amount of counter pressure is encountered, to prevent pumping fluid with a total occulation in the IV line, any significant encumberance on the pump motor shaft will cause the pump to malfunction. Such malfunction can occur in the above identified patent's design by the intentional or unintentional application of some exigent force being exerted on the pump motor shaft such as another piece of equipment falling on the shaft.

Another problem, not addressed in any prior art, concerns the inability of any previously known pump to interface with digitally controlled medical equipment or instruments. This lack of an ability to interface prevents the peristaltic pump from operating in conjunction with other digitally controlled medical equipment without the need for human monitoring.

Another problem not addressed in any prior art deals with the pumps total lack of any self-diagnostic operations. It is only through constant and costly human maintenance that a pump can be properly maintained such that it is reliably safe under all use conditions.

SUMMARY OF THE PRESENT INVENTION

It is therefore an object of the present invention to provide a peristaltic pump-disposable cassette design which utilizes an uncomplicated and economical design.

It is a further object of the present invention to provide an improved peristalic pump-disposable cassette system design which utilizes an improved cassette loading/unloading apparatus such being designed for rapid and efficient operation under emergency conditions.

It is a further object of the present invention to provide an improved peristalic pump-disposable cassette system which utilizes a simple economical means by which to cause the peristalic action on a section of elastic tubing without generating any unintended distortion or migration of said tube over the pump rotor assembly.

It is also an object of the present invention to provide an improved peristaltic pump-disposable cassette system which utilizes a simple and economically feasible means by which to quickly determine whether or not the cassette is in its operational position.

It is also an object of the present invention to provide an improved peristaltic pump-disposable cassette system which utilizes a simple and economically feasible means for preventing pump failure due to battery or IV tube leakage.

It is also an object of the present invention to provide an improved peristaltic pump-disposable cassette system design which utilizes a means for protecting the pump motor shaft from external interference.

It is also an object of the present invention to provide an improved peristaltic pump-disposable cassette system which utilize a means for self-diagnosis operations and a means to interface with digitally controlled medical equipment and monitoring instruments.

Briefly, a preferred embodiment of the present invention includes an improved disposable cassette and an improved peristaltic infusion pump. The disposable cassette consists of a rigid asymmetrical cartridge and a continuous hollow conduit arrangement adapted to pass IV fluids therethrough. The continuous hollow conduit includes a translucent hollow molded plastic connector joined to one end of a section of elastic tubing and another (nontranslucent) connector joined to the opposite end of the tubing. The hollow conduit arrangement is mounted in the cassette cartridge which is designed to house the two connectors and support both ends of the elastic tubing while prestressing and suspending the intermediate portion of said tube. In this arrangement, the tube has uninterrupted movement in a direction perpendicular to the base of the cartridge and is located in a readily accessible position. The peristaltic pump includes a housing to enclose necessary pump mechanisms and electronics and a pump cassette housing arrangement to provide a means for properly aligning and supporting the cassette. The pump cassette housing is located to the side of the pump housing. Internal to the pump cassette housing is the pump rotor assembly which when in use compresses and releases the elastic tubing of the cassette in rapid succession so as to propagate a peristaltic pumping force. Internal to the pump mechanism is a microprocessor which controls the pump functions, performs self-diagnostic pump operations and provides the pump with an ability to interface with other digitally controlled equipment and/or instruments. Beneath the pump, forming its base, is an external auxilliary battery.

An advantage of the present invention is that the design of the cassette-pump rotor assembly, interface prevents migration of the elastic tubing around the pump rotor assembly thereby greatly increasing the accuracy with which the pump administers IV fluids to a patient.

Another advantage of the present invention is that the improved pump cassette housing provides a simple, easy to use means by which to quickly load or unload the disposable cassette.

Another advantage of the present invention is that the components are designed to be more cost effective than prior art, making the present invention less expensive for the end purchaser, while increasing the pumps operational performance.

Another advantage of the present invention is the use of a microprocessor to control pump functions and facilitate interface with other digitally controlled medical equipment and instruments.

Another advantage of the present invention is that even an inexperienced pump operator can easily determine when the cassette is in its operational position. This advantage is realized because the cassette will only remain in an operational position while it is engaged by the pump rotor assembly. Once the cassette is disengaged from the rotor assembly, the tension created by the rotors' compression of the elastic tube forces the cassette out of the operational position causing the ejection of the cassette from the pump cassette housing.

Another advantage of the present invention is that the rotation of the pump's motor shaft cannot be inhibited due to its total enclosure by the pump housing.

Another advantage of the present invention is that any leakage caused by poorly maintained or faulty batteries, IV tubes, or disposable cassettes will not interfere with the pump operations due to the unique placement of the battery and pump cassette housing with regard to the internal pump mechanisms.

These and other objects and advantages of the present invention will no doubt become apparent to those skilled in the art after having read the following detailed description of the preferred embodiment which is illustrated in the various drawing figures.

DETAILED DESCRIPTION OF THE PREFERRED EMBODIMENT

Figures 1, 3:
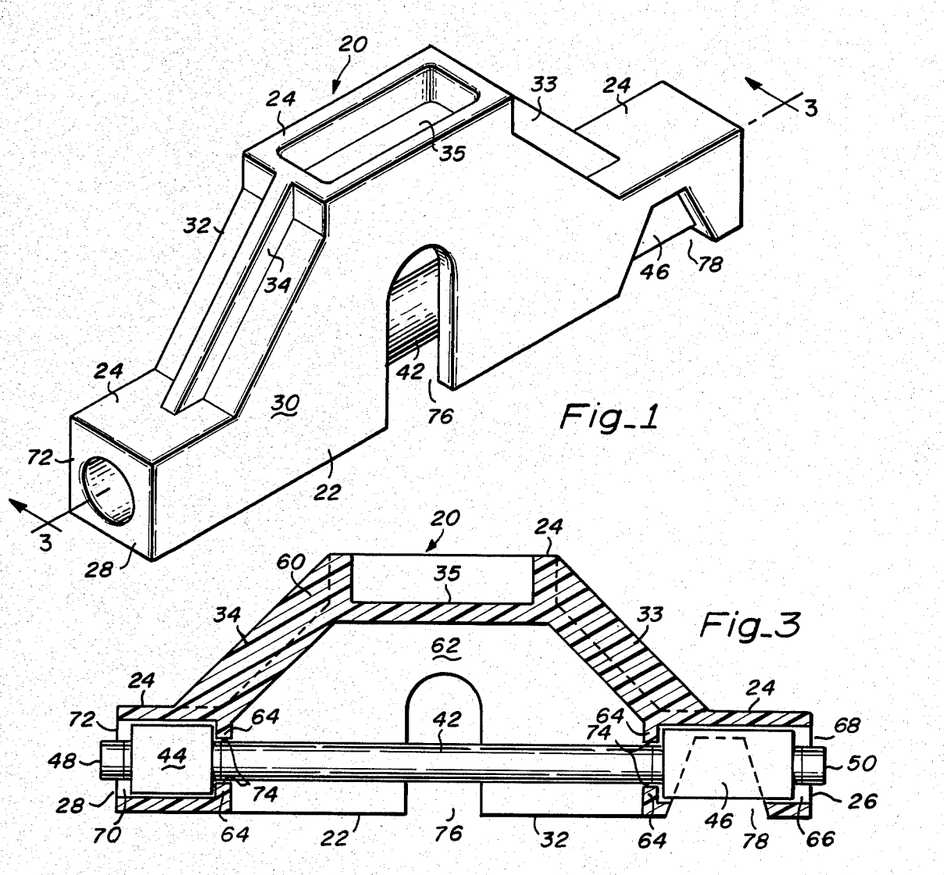
FIG. 1 is a perspective view of a disposable cassette according to the present invention.
FIG. 3 is a cross-sectional view of the disposable cassette of FIG. 1 taken along the line 3—3.

Referring to FIG. 1 there is illustrated a disposable cassette referred to by the general reference character 20 and designed for use with a peristaltic infusion pump, to be described hereafter. Cassette 20 is designed to pass IV fluids under peristaltic pressure. Cassette 20 includes a base surface 22, a top surface 24, a right side wall 26, a left side wall 28, a front side wall 30, a rear side wall 32, a right sloping angular structural buttress 33, a left angular sloping structural buttress 34, and an indented top 35.

Figures 2, 4, 5:
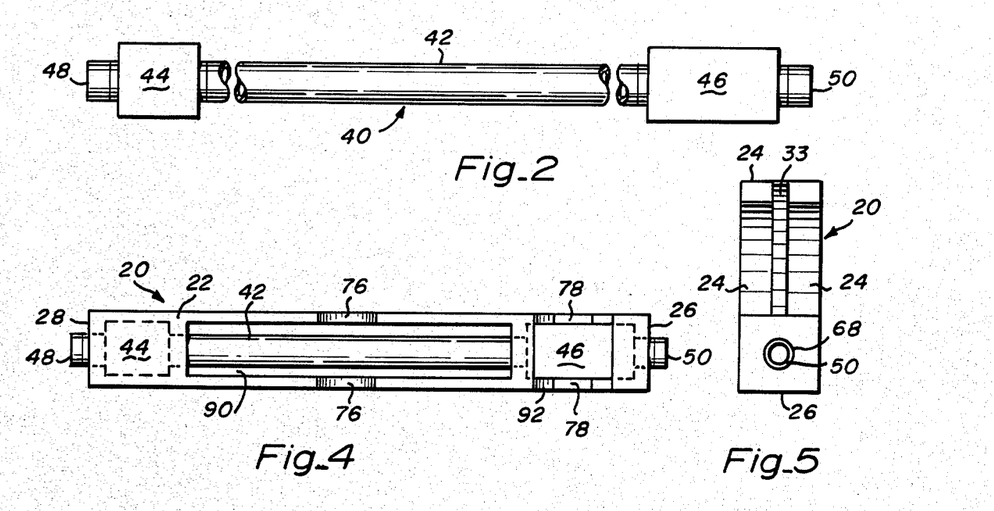
FIG. 2 is a side view of a three-piece hollow conduit arrangement comprising part of the cassette of FIG. 1.
FIG. 4 is a bottom view of the disposable cassette of FIG. 1.
FIG. 5 is a side view of the disposable cassette of FIG. 1.

Referring to FIG. 2 a conduit arrangement referred to by the general reference character 40 is shown unassembled for the purposes of description. The conduit 40 serves to provide a leak proof passageway through which IV fluids can be passed. Conduit arrangement 40 includes a section of elastic tubing 42, a first tubular connector 44, of common design with opposite ends capable of forming leak proof tubular junctions, and a second tubular connector 46, of a unique translucent hollow molded plastic design having opposite ends capable of forming leak proof tubular junctions. Elastic tube 42 is the only component of cassette 20 directly subjected to peristalic action. Elastic tube 42 is of a predetermined length, so that when mounted in a cassette cartridge (to be defined hereafter) tube 42 will be subject to longitudinal stress. Elastic tube 42 must be of sufficient quality to withstand the tubular distortions associated with prolonged exposure to peristaltic action. Tube 42 must be sufficiently supple to ensure that proper compression is achieved when peristalic action is applied.

As shown in FIG. 2 tubular connector 44 is positioned so that one of its end portions is fixedly joined to an end portion of elastic tube 42. The other end portion of connector 44 is joined, in a detachable manner, to an end portion of an IV tube 48 which connects to an IV reservoir (not shown). A second tubular connector 46 is positioned so that one of its end portions is permanently joined to the free end portion of elastic tube 42. The other end portion of the connector 46 is joined, in a detachable manner, to an end portion of an IV tube 50 which connects cassette 20 with an IV needle (not shown).

FIG. 3 illustrates a cross-section view of cassette 20 taken along line 3—3 of FIG. 1. Cassette 20 includes a rigid cassette cartridge 60 and hollow conduit arrangement 40. Cartridge 60 provides a means for mounting the hollow conduit arrangement 40. Cassette cartridge 60 is a single piece rigid plastic structure which may be formed by use of an injection mold process. Cartridge 60 contains three internal cassette chambers including a first cassette chamber 62, bounded by front cassette wall 30, rear cassette wall 32, cassette base 22, cassette top wall 35, and internal flanges 64; a second cassette chamber 66, bounded by front cassette wall 30, rear cassette wall 32, cassette base 22, cassette top 24, internal flange 64 and the outer most edge of a right side opening 68; and a third cassette chamber 70, bounded by front cassette wall 30, rear cassette wall 32, cassette base 22, cassette top 24, flange 64 and the outer most edge of a left side opening 72. The connector 44 is mounted in the cassette chamber 72, the connector 46 is mounted in the cassette chamber 66 and the intermediate portion of elastic tube 42 is suspended, under longitudinal stress, in the cassette chamber 62. The end portions of tube 42 are connected, as previously described, with the connectors 44 and 46 and pass through a set of tubular passageways 74.

Incorporated in front cassette wall 32 and rear cassette wall 30 is a U-shaped opening 76 for a pump shaft (to be defined) and a slot 78 forming a bubble detector opening. The opening 76 is located in an off center position, as shown in FIG. 3, in both cassette wall 32 and rear cassette wall 30 and extends to approximately three-quarters of the height of the chamber 62. The opening 76 is located in the walls 30 and 32 so as to be directly aligned with each other. The opening 76 is designed to expose for ready access, a portion of the tube 42. The bubble detector slot 78 is located adjacent to the connector 46 in front cassette wall 32 and rear cassette wall 30 and exposes the majority of second connector 46 on both sides of cassette 20. The connector 46 is preferably transparent and exposed so that IV fluids passing through it may be analyzed by a monitoring device (to be described hereafter) utilized to detect air bubbles or other impurities contained within the IV fluid.

FIG. 4 illustrates a bottom view of cassette 20 illustrating two rectangular openings 90 and 92. The rectangular opening 90, exposes a substantial portion of elastic tube 42. The rectangular opening 92 is directly below the connector 46 and forms a bottom bubble detector opening which exposes a majority of the bottom portion of second connector 46.

FIG. 5 illustrates a right side elevational view of the disposable cassette 20.

The structural design of cartridge 60 allows it to be fabricated as a single rigid structure resulting in low manufacturing costs. The single piece fabrication of cartridge 60 also results in low material cost as the fabrication of a single piece structure can generally be achieved with the use of less materials than a comparable multisection structure. Furthermore, low material and manufacturing costs are maintained by the design of the hollow conduit arrangement 40 which uses only two connectors and one piece of elastic tubing. In more conventional designs such arrangements require a plurality of connectors and hollow tubes. Furthermore, the design of cassette cartridge 60 provides that connector 44 and/or connector 46 can be easily inserted or removed from their respective chambers 70 and 66. The advantage to such a design includes the fact that low assembly costs are incurred when hollow conduit arrangement 40 is mounted in cassette cartridge 60, and faulty or leaking connectors can easily be removed and replaced in emergency situations if another cassette 20 is not readily available. Further, design of cassette 20 provides for the intermediate section of elastic tube 42 to be suspended in cassette chamber 62 in such a way as to prestress elastic tube 42 while allowing tube 42 free uninterrupted motion in a direction perpendicular to cassette base 24. This prevents creeping or undue distortion or stretching of elastic tube 42. This is due to the fact that tube 42 is not supported or backed by any structure, allowing tube 42 to more evenly ride over a pump rotor assembly (to be described hereinafter) instead of being subjected to the more conventional design of squeezing elastic tube 42 against a backing structure to generate the peristaltic pressure. The reduction in the creeping, and undue abuse of tube 42 results in very accurate IV pressures and flow rates.

Figure 6:
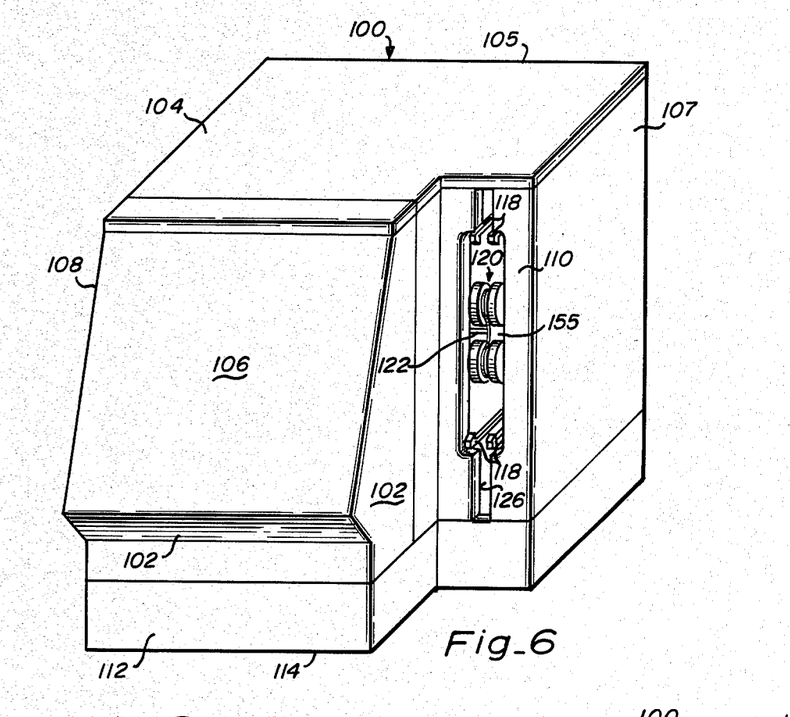
FIG. 6 is a perspective view of a peristaltic infusion pump according to the present invention.
Figures 7, 8:
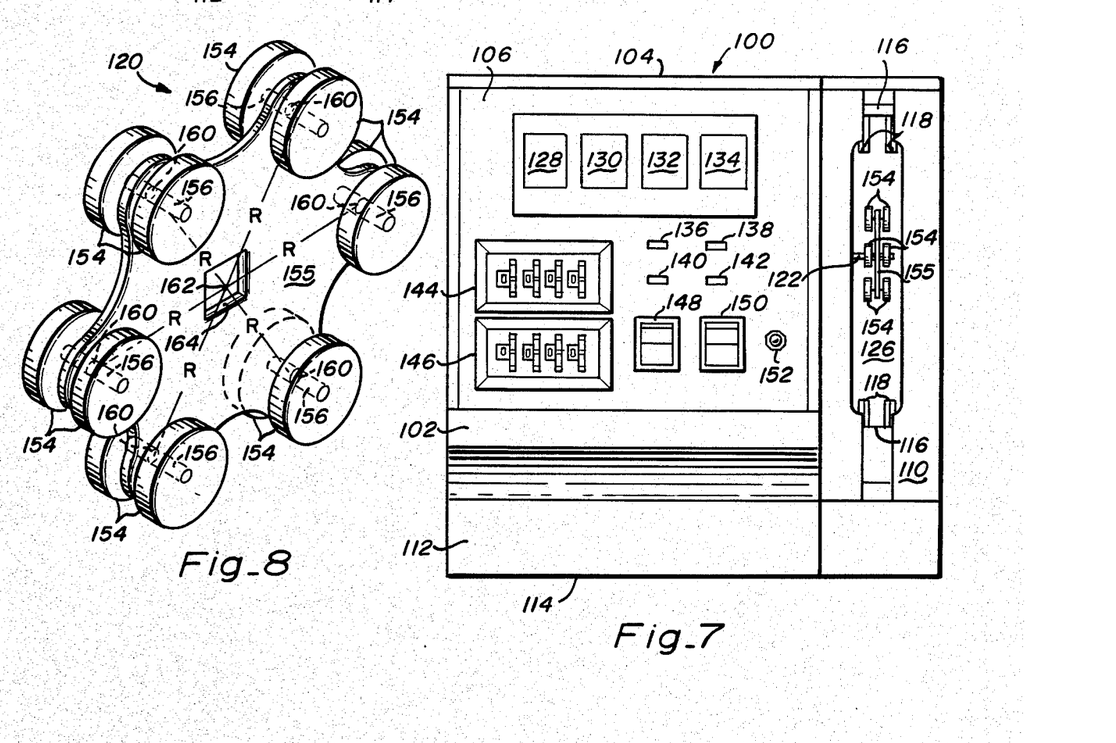
FIG. 7 is a frontal view of the peristaltic pump of FIG. 6.
FIG. 8 is a perspective view of a pump rotor assembly according to the present invention.

Attention is now directed to FIGS. 6 and 7 which illustrate a peristaltic infusion pump 100 which, along with cassette 20, comprises part of an overall peristaltic infusion pump assembly. FIG. 6 is a perspective view of the pump 100 and FIG. 7 is a frontal view of the pump 100. The pump 100 has a pump housing 102, wherein all mechanical and electrical components are located; a pump housing top cover 104; a rear side wall 105; a front pump panel 106, which supports a variety of switches and indicators; a left side wall 107; a right side wall 108; a pump cassette housing 110, which supports, aligns and locks cassette 20 into its proper operational position; an auxillary battery chamber 112 and a base member 114 for the pump housing 102. Pump cassette housing 110 encloses a cassette locking mechanism 116. Cassette locking mechanism 116 includes a set of four spring loaded metallic locking hooks 118. Locking hooks 118 are designed to articulate around a pivot point to allow locking hooks 118 to lock or release cassette 20. Also enclosed in pump cassette housing 110 is a pump rotor assembly 120 and a pump rotor shaft 122 to connect a pump motor 124 (see FIG. 9) to the pump rotor assembly 120. Pump cassette housing 110 also incorporates a cassette slot 126 running the vertical length of the front of pump cassette housing 110. Cassette slot 126 is designed to be narrower at its end portions than in its mid section. The width of mid section of cassette slot 126 is sufficient to allow easy insertion or extraction of cassette 20. Furthermore, cassette slot 126 extends into pump cassette housing 110 to a predetermined distance of approximately ⅝ths of the length of cassette 20.

The front panel 102 includes a set of indicators. Such indicators include a COMPLETE OCCLUSION indicator 128, an AIR in-line indicator 130, a LOW BATTERY indicator 132, an ON BATTERY indicator 134, an ENTER VOLUME indicator 136, a RATE TO 100 indicator 138, an ENTER RATE indicator 140, and a REDUCE RATE indicator 142. Front pump panel 106 also supports a set of switches which include a VOLUME switch 144, a RATE switch 146, an ON/RESET switch 148, a RUN/STOP switch 150, and an EJECT switch 152.

Figure 9:
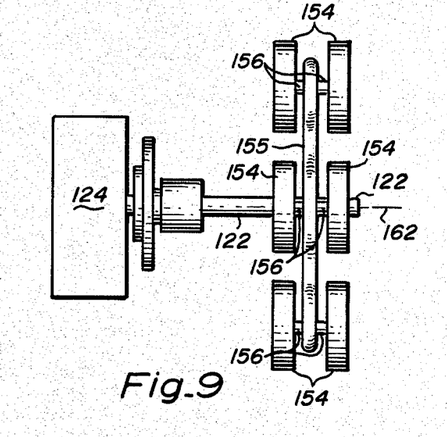
FIG. 9 is a frontal view of the pump rotor assembly of FIG. 8.
Figure 10:
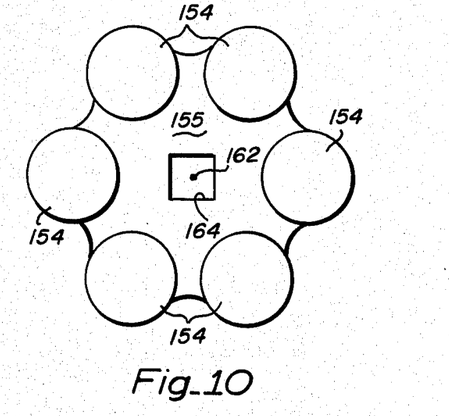
FIG. 10 is a side view of the pump rotor assembly of FIG. 8.

FIG. 8, 9 and 10 depict the pump rotor assembly 120 which includes a plurality of short cylindrical rollers 154 attached to a pump rotor plate 155 by a plurality of short roller shafts 156 which are fixedly connected to the rollers 154 and pass through pump roller plate 155 via a set of predetermined holes 160. The plate 155 rotates about its axis 162. In the preferred embodiment of the present invention, the predetermined roller shaft holes 160 are arranged at the circumference of a circular pattern of radius "R" and coaxial with the axis 162 of the pump rotor plate 155. Rollers 154 are of such a radius and placement that they marginally extend past the peripheral edge of pump roller plate 155. For this reason, rollers 154, but not plate 155, contact elastic tube 42 when pump 100 and cassette 20 are functioning properly. About the axis 162 of the plate 155 is a square pump shaft hole 164 through which pump shaft 122 passes to connect pump rotor assembly 120 to pump motor 124.

Various advantages of the aforementioned design are as follows. Pump housing 102, due to the placement of pump cassette housing 110 and the unique structure of disposable cassette 20, occupies less space and is lighter than more conventional pump housing designs. Also, the placement of pump cassette housing 110 to the side of pump housing 102, provides assurance that no pump malfunction can occur due to fluid leakage resulting from faulty IV tube connections or disposable cassette 20 malfunctions. In addition, auxiliary battery chamber 112 attached to the bottom of pump housing 102, which forms a base 114 for pump housing 102, is positioned such that any external leakage of corrosive solvents from a battery in chamber 112 will not intrude upon internal pump mechanisms and result in pump malfunctions. Furthermore, the placement of battery chamber 112 in an external position to pump housing 102 enhances the ability of a pump operator to easily change the battery and replace it with either a new battery or a battery of increased service life, thereby enabling pump assembly 100 to be utilized for extended periods of time without the need for an external power supply. Furthermore, use of pump rotor assembly 120, according to the preferred embodiment, allows the present invention to utilize a slim, low cost and easy to manipulate disposable cassette thereby increasing the overall efficiency of the present invention.

Figure 11:
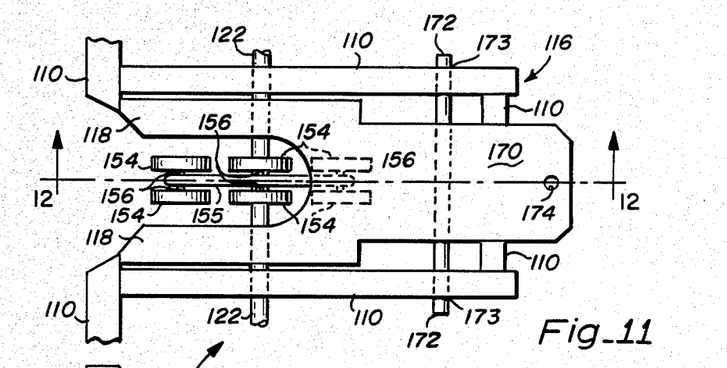
FIG. 11 is a top view of the locking assembly according to the present invention.
Figure 12:
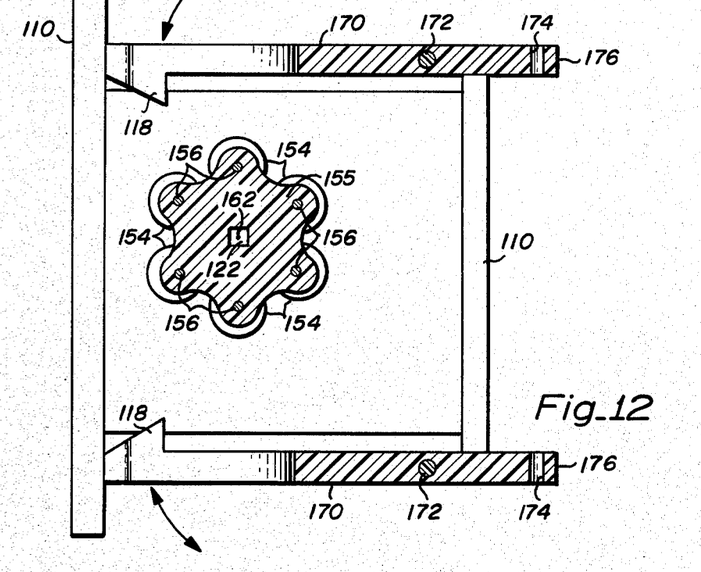
FIG. 12 is a cross sectional view of the locking assembly taken along line 12—12.

Focus is now directed toward FIGS. 11 and 12. FIG. 11 illustrates a top view of the cassette locking mechanism 116 which includes a portion of pump cassette housing 110, the locking hooks 118, and locking hook arms 170 connected to pump cassette housing 110 via pivot shafts 172. The arms 170 are designed to articulate around pivot shafts 172 as illustrated in FIG. 12. Pivot shaft 172 is fixedly mounted in pump cassette housing 110 (not shown) and passes through a pivot shaft opening 173 located at a predetermined position in arms 170. Another opening 174 is provided in each arm 170 to facilitate the mounting of either a manual or electromechanic opening device (not shown). Such an opening device would cause the rear ends of the arms 176 to move toward each other whereby the locking hooks 118 would be forced open to release cassette 20 when such is locked in its operative position against pump rotor assembly 120.

Figure 13:
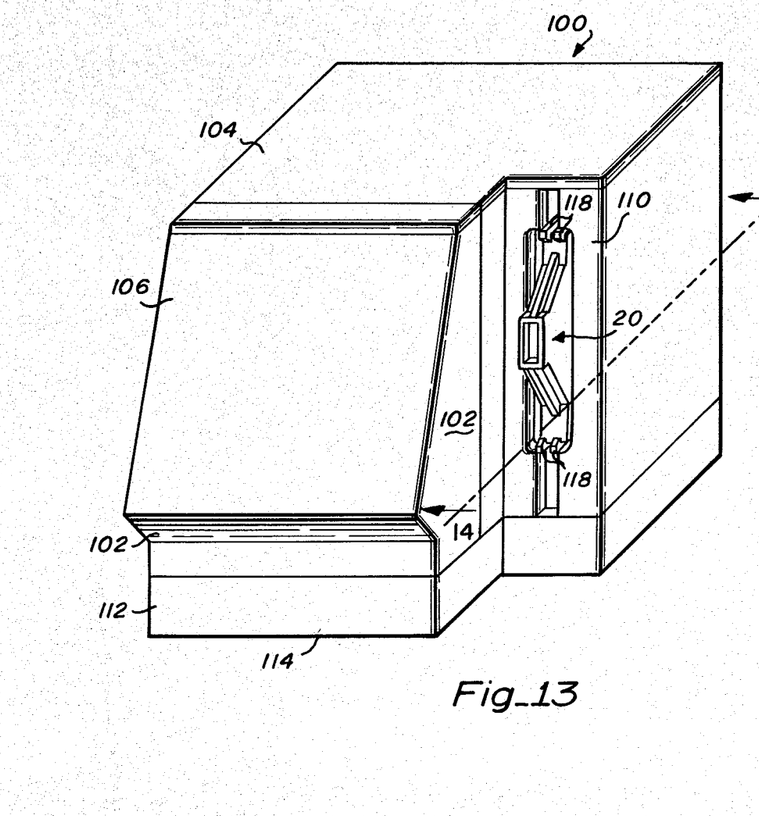
FIG. 13 is a prospective view of the peristaltic infusion pump with the disposable cassette in operating position.
Figure 14:
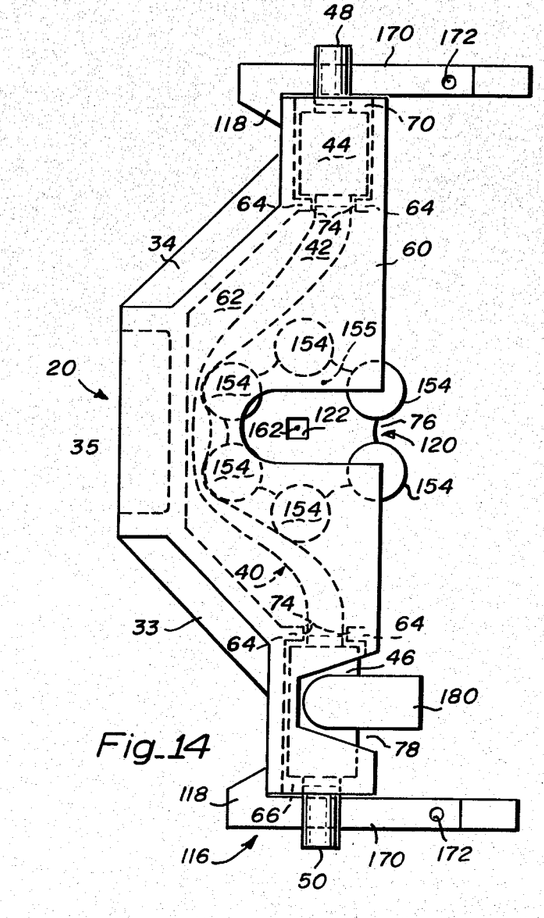
FIG. 14 is an enlarged cross sectional view of the disposable cassette engaged in its operative position within the pump cassette housing taken along line 14—14 of FIG. 13.

Attention is now turned to the process by which pump 100 and cassette 20 interact to produce the desired peristaltic action. Specific attention is directed towards FIG. 13-16 which illustrate different views of cassette 20 relative to pump cassette housing 110. FIG. 13 illustrates a perspective view of cassette 20 engaged in pump cassette housing 110. FIG. 14 depicts a cross-section view of cassette 20 engaged in pump cassette housing 110 taken along line 14—14 of FIG. 13. In FIG. 14, cassette locking hooks 118 and arms 170 are shown holding disposable cassette 20 in pump cassette housing 110 (not shown). Locking mechanism 116 is required in the preferred embodiment due to the spring tension created when elastic tube 42 is stretched around pump rotor assembly 120 as illustrated in FIG. 14.

In operation, pump rotor assembly 120 rotates in a counter-clockwise direction rhythmically compressing and releasing elastic tube 42. The interface between pump rollers 154 and elastic tube 42 cause propagation of the desired peristaltic pressure which motivates the IV fluid in elastic tube 42. Each time one set of rollers 154 comes in contact with elastic tube 42 in this fashion, rollers 154 gradually compresses elastic tube 42 until total occulation of tube 42 occurs. When total occulation of tube 42 has occurred and pump rollers 154 continue their counter-clockwise rotation, all IV fluid in front of rollers 154 is propelled forward toward the patient. The preferred embodiment of the present invention does not use any backing structure to stabilize or constrain elastic tube 42. Use of any such structure would precipitate a migration of tube 42 around pump rotor assembly 116 resulting in undesirable pressure and flow inaccuracies.

As previously discussed, the preferred embodiment incorporates monitoring means to monitor the IV fluid passing through hollow conduit arrangement 40 for air bubbles and other fluid impurities. To accomplish this bubble detection, an index of refraction monitor 180 is used. Monitor 180 is located in pump cassette housing 110 and is positioned adjacent to bubble opening 78 so as to be adjacent to second connector 46 when cassette 20 is properly inserted into pump cassette housing 110. (See FIG. 14).

Figures 15, 16, 17:
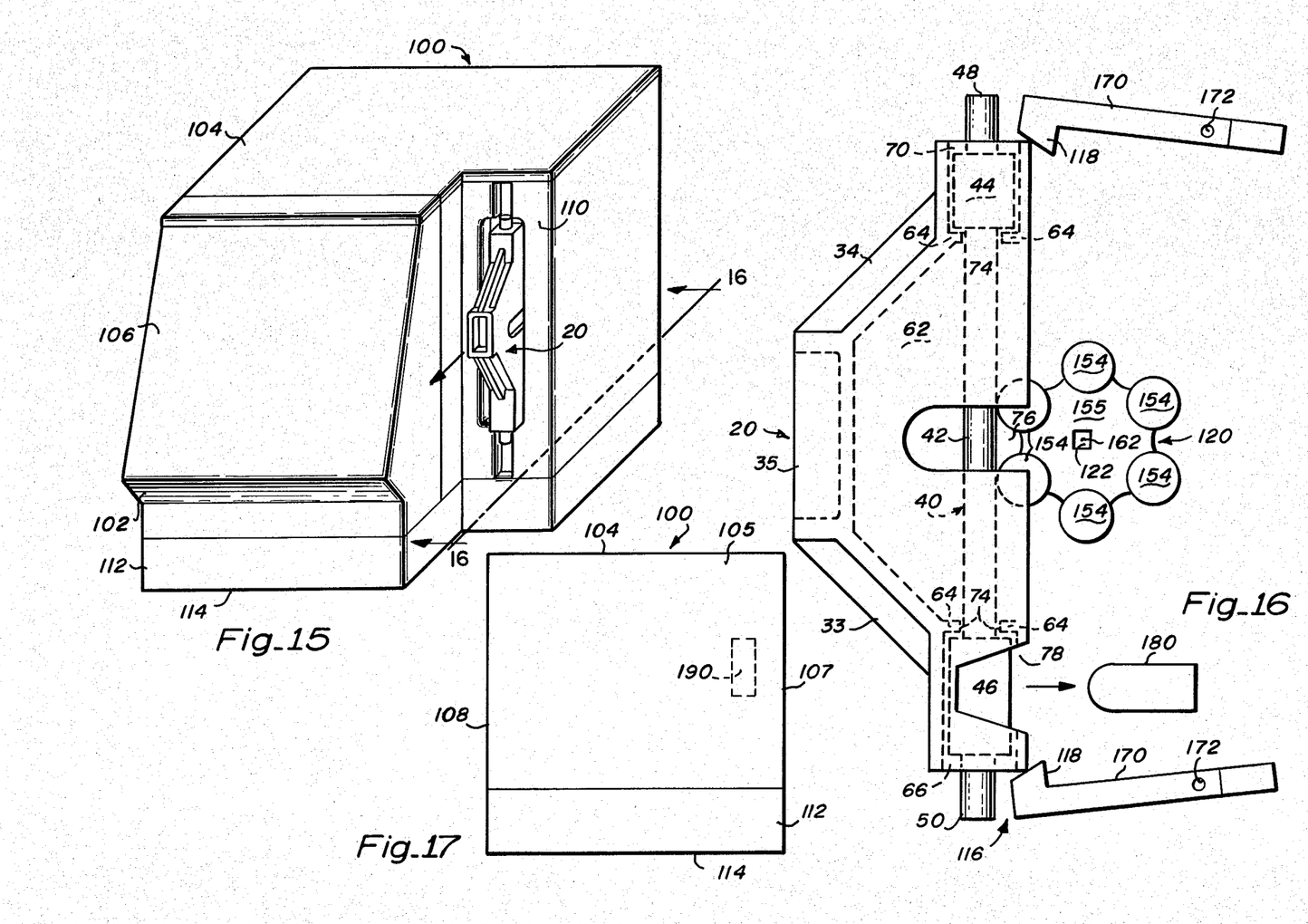
FIG. 15 is a perspective view of the peristaltic infusion pump with the disposable cassette in the pump cassette housing, but, not engaged in its operative position.
FIG. 16 is an enlarged view of the disposable cassette disengaged from the pump rotor assembly, but, still resting in the cassette housing taken along line 16—16 of FIG. 15.
FIG. 17 is a rear view of the peristaltic infusion pump.

FIG. 15 shows cassette 20 resting on pump cassette housing 110 in an inoperative position and FIG. 16 depicts a cross-sectional view of such taken along line 16-16 of FIG. 15. In FIG. 16, cassette 20 is not held in position by locking assembly 116, but rests on top of locking hooks 118. Elastic tube 42 is not stretched or distorted by pump rotor assembly 120 and second connector 46 is not adjacent to index of refraction monitor 180. In this position, no peristaltic pressure is generated in the tube 42. Also in this position, and whenever IV tube 48 and IV tube 50 are properly connected to cassette 20, the IV fluid can be gravitationally administered to patient without aid of pump assembly 100.

Various advantages attributed to the present invention include the fact that no complex mechanical apparatus is required to position, align or insert cassette 20 into pump cassette housing 110. In the preferred embodiment cassette 20 is positioned at the opening of cassette slot 126 and manually inserted into pump cassette housing 110 wherein locking mechanism 116 engages cassette 20 to secure it into position. The release of cassette 20 is performed just as easily. A mechanical or electromechanical arrangement (not shown) is utilized to release locking mechanism 116. Once cassette 20 is released, it is ejected from cassette pump housing 110 using the stored kinetic energy of stretched elastic tube 42 as a means of motivating cassette 20 from pump cassette housing 110. This simple loading/unloading arrangement provides a low cost solution to two unresolved problems associated with the use of conventional peristalic infusion pumps. First, this system furnishes the pump operator with a simple, fool-proof method for loading/unloading cassette 20 even in urgent situations. Also, this unique design provides an inexperienced pump operator with a quick way to determine if cassette 20 is or is not in its operative position. If cassette 20 is positioned as shown in FIG. 13, cassette 20 is engaged. If most of cassette 20 is exposed, as shown in FIG. 15, cassette 20 is disengaged and no peristaltic pumping action will transpire.

The pump 100 and its function has been described without regard to various electrical components which are necessary to its operation. For purposes of the present invention, it is understood that these electrical components and most electrical circuitry necessary for the operation of pump 100 may be conventional. A microprocessor 190, shown in FIG. 17 which illustrates a rear view of pump 100, is utilized so as to provide the pump with additional advantages over conventional design. By using a microprocessor to control pump 100 operations, certain advantages are realized, such as, the ability of pump 100 to interface with other digitally controlled machines or medical instruments and to provide self-diagnostic safeguard functions to insure proper pump operations. The electrical circuitry for operating pump 100 could include suitable circuitry to energize and power pump motor 124; increase or decrease the speed of pump motor 124 dependent upon desired IV flow rate; deenergize pump motor 124 upon administration of a predetermined quantity of IV fluids; monitor the quantity and flow rates for IV fluids; provide a means to monitor the IV fluids for bubbles or other impurities; and to deenergize pump motor 124 and/or alert a pump operator, when such are determined to be present in the IV fluid; and to monitor and run the front panel monitor indicators.

Although the present invention has been described in terms of the presently preferred embodiment(s), it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

I claim:

1. A peristaltic pump assembly, comprising:
a pump arrangement including a pump cassette housing having portions defining a vertical cassette aperture located adjacent a pump housing enclosing a pump mechanism, said pump cassette housing having means for supporting and aligning a disposable cassette in an operative position relative to said pump mechanism, said pump mechanism having securing means for securing said disposable cassette within said pump cassette housing and a locking mechanism to securely support and retain said cassette in an operative position relative to said securing means while said cassette is positioned in said pump cassette housing, said locking mechanism including a plurality of locking arms and hooks with each arm articulating about a pivot shaft connecting said pump cassette housing with each locking arm and one of said locking hooks located on each locking arm to physically restrain said cassette in its operative position relative to said pump mechanism, and means located in said pump cassette housing for cooperating with said cassette in a predetermined manner for peristaltically pumping fluid; said cassette having a hollow conduit arrangement including a predetermined length of elastic tubing and first and second connectors with opposite end portions of said tubing being joined to said first and second connectors forming leak-proof junctions with said tubing such that fluid may be pumped through said hollow conduit arrangement; said cassette further including a single piece cartridge structure of dimensions for fitting in said cassette aperture and being supported by said pump cassette housing having a first means for removably mounting an end portion of said first connector and a second means for removably mounting an end portion of said second connector to permit removal aand replacement of said connectors without dismantling said cartridge, and said tubing being tautly suspended and accessible to said pump mechanism along a portion of the base of said cartridge structure so that said tube is longitudinally elongated in a predetermined manner when fitted in the pump cassette housing; said cassette including a U-shaped pump shaft opening symetrically positioned along at least one side of said cartridge to expose a predetermined length of said elastic tubing; said U-shaped pump shaft opening located in an off-center position in the wall of said cartridge structure to expose a predetermined section of said tubing; wherein said operative position of the cassette causes said tube to be longitudinally elongated about the pump rotor rollers so that peristaltic pumping can be accomplished on said tube, and said elongated tube creates a springlike tension on said cassette cartridge such that said cassette cartridge is forced out of the pump cassette housing if not restrained.

2. A peristaltic pump according to claim 1 wherein, said pump mechanism includes microprocessor means for monitoring the index of refraction of fluid passing through said hollow conduit arrangement for monitoring fluid flow through said hollow conduit arrangement and for providing control signals to said pump mechanism responsive to said monitor signals; and
said cartridge structure is a rigid asymmetrical structure with first and second end portions connected to an intermediate raised section with a first angular structural support buttress located between said first end portion and said intermediate section and a second angular structural support buttress located between said second end portion and said raised intermediate section.

3. A peristaltic pump assembly, comprising:
a pump arrangement including a pump cassette housing having portions defining a vertical cassette aperture located adjacent a pump housing enclosing a pump mechanism, said pump cassette housing having means for supporting and aligning a disposable cassette in an operative position relative to said pump mechanism, said pump mechanism having securing means for securing said disposable cassette within said pump cassette housing and a locking mechanism to securely support and retain said cassette in an operative position relative to said securing means while said cassette is positioned in said pump cassette housing, said locking mechanism including a plurality of locking arms and hooks with each arm articulating about a pivot shaft connecting said pump cassette housing with each locking arm and one of said locking hooks located on each locking arm to physically restrain said cassette in its operative position relative to said pump mechanism, and means located in said pump cassette housing for cooperating with said cassette in a predetermined manner for peristaltically pumping fluid; said cassette having a hollow conduit arrangement including a predetermined length of elastic tubing and first and second connectors with opposite end portions of said tubing being joined to said first and second connectors forming leak-proof junctions with said tubing such that fluid may be pumped through said hollow conduit arrangement; said cassette further including a single piece cartridge structure of dimensions for fitting in said cassette aperture and being supported by said pump cassette housing having a first means for removably mounting an end portion of said first connector and a second means for removably mounting and end portion of said second connector to permit removal and replacement of said connectors without dismantling said cartridge, and said tubing being tautly suspended and accessible to said pump mechanism along a portion of the base of said cartridge structure so that said tube is longitudinally elongated in a predetermined manner when fitted in the pump cassette housing; said cassette including a U-shaped pump shaft opening symmetrically positioned along at least one side of said cartridge to expose a predetermined length of said eleastic tubing; said U-shaped pump shaft opening located in a horizontally off-center position in the wall of said cartridge structure to expose a predetermined section of said tubing; wherein said operative position of the cassette causes said tube to be longitudinally elongated about the pump rotor rollers so that peristaltic pumping can be accomplished on said tube, and said elongated tube creates a spring-like tension on said cassette cartridge such that said cassette cartridge is forced out of the pump cassette housing if not restrained.

4. A peristaltic pump assembly, comprising:
a pump arrangement including a pump cassette housing having portions defining a vertical cassette aperture located adjacent a pump housing enclosing a pump mechanism, said pump cassette housing having means for supporting and aligning a disposable cassette in an operative position relative to said pump mechanism, said pump mechanism having means for securing said disposable cassette within said pump cassette housing, and means located in said pump cassette housing for cooperating with said cassette in a predetermined manner for peristaltically pumping fluid; said cassette having a hollow conduit arrangement including a predetermined length of elastic tubing and first and second connectors with opposite end portions of said tubing being joined to said first and second connectors forming leak-proof junctions with said tubing such that fluid may be pumped through said hollow conduit arrangement; said cassette further including a single piece cartridge structure of dimensions for fitting in said cassette aperture and beng supported by said pump cassette housing having a first means for removably mounting an end portion of said first connector and a second means for removably mounting an end portion of said second connector to permit removal and replacement of said connectors without dismantling said cartridge, and said tubing being tautly suspended and accessible to said pump mechanism along a portion of the base of said cartridge structure so that said tube is longitudinally elongated in a predetermined manner when fitted in the pump cassette housing; said cartridge structure further including a rigid assymetric structure having first and second end portions connected by an intermediate raised section with a first angular structural support buttress located between said first end portion and said intermediate raised section and a second angular structual support buttress located between said second end portion and said raised intermediate section, and U-shaped pump shaft openings symmetrically located in a horizontally off-center position along each wall of said cartridge structure to expose a predetermined length of said plastic tube and means for exposing a portion of the sides and base of said second connector; said pump mechanism further including a pump rotor assembly for generating the peristaltic pressure in said cassette, said pump rotor assembly including a pump rotor plate having a coaxial pump rotor shaft opening and a plurality of disk-shaped rollers mounted on said plate, said rollers being mounted in pairs with one on each side of said plate and each pair of rollers being equally spaced about said pump plate axis at a predetermined radius whereby said rollers laterally extend past said plate so that any structure contacting said rollers does not interfere with said pump rotor plate; and said means for suspending said tubing includes means for allowing said tube to move in a perpendicular direction relative to said cassette; said pump mechanism further including a locking mechansim to securely support and retain said cassette in its operative position while said cassette is in said pump cassette housing, said locking mechanism having a plurality of locking arms and hooks, each of said arms articulating about a pivot shaft connecting said pump cassette housing to each locking arm and one of said locking hooks, located on each said locking arm to physically retain said cassette in its operative position relative to said pump mechanism, and said pump mechanism also includes a microprocessor means for monitoring the index of refraction of fluid passing through the hollow conduit arrangement and for providing control signals to said pump mechanism responsive to said monitor signals, said pump housing also includes means for storing an auxilliary battery, said battery being connected to said pump mechanism to power said pump mechanism when a main power supply is unavailable; and said pump cassette housing including a front panel supporting an OCCLUSION indicator, an AIR indicator, a LOW BATTERY indicator, an ON BATTERY indicator, an ENTER VOLUME indicator, a RATE TO 100 indicator, an ENTER RATE indicator, a REDUCE RATE indicator, a VOLUME switch, a RATE switch, an ON/RESET switch and an EJECT switch.

5. An improved peristaltic pump assembly, comprising:
a pump arrangement including a pump cassette housing located aside a pump housing enclosing a pump mechanism comprising a pump rotor assembly for generating peristaltic pressure in said cassette, said pump rotor assembly having a pump rotor plate with a coaxial pump rotor shaft opening and a plurality of disk-shaped rollers mounted on said plate, said rollers being mounted in pairs with one on each side of said plate and each pair of rollers being equally spaced about said pump plate axis at a predetermined radius whereby said rollers laterally extend past said plate so that any structure contacting said rollers does not interfere with said pump rotor plate; and said means for suspending said tubing includes means for allowing said tube to move in a perpendicular direction relative to said cassette base, said pump cassette housing having means for supporting and aligning a disposable cassette in an operative position relative to said pump mechanism, said pump mechanism having means for securing said disposable cassette within said pump cassette housing, means located in said pump cassette housing for cooperating with said cassette in a predetermined manner for peristaltically pumping fluid; said cassette having a hollow conduit arrangement including a predetermined length of elastic tubing and first and second connectors with opposite end portions of said tubing being joined to said first and second connectors and forming leak-proof junctions with said tubing such that fluid may be pumped through said hollow conduit arrangement; said cassette further including a cartridge structure of dimensions for fitting in and being supported by said pump cassette housing and having a first means for mounting an end portion of said first connector and a second means for mounting an end portion of said first connector and a second means for mounting an end portion of said second connector with said tubing being tautly suspended and accessible to said pump mechanism along a portion of the base of said cartridge structure;

said pump cassette housing including a front panel supporting an OCCLUSION indicator, an AIR indicator, a LOW BATTERY indicator, an ON BATTERY indicator, an ENTER VOLUME indicator, a RATE TO 100 indicator, an ENTER RATE indicator, a REDUCE RATE indicator, a VOLUME switch, a RATE switch, an ON/RESET switch and and EJECT switch;

said pump mechanism including a locking mechanism to securely support and retain said cassette in its operative position while said cassette is in said pump cassette housing, said locking mechanism having a plurality of locking arms and hooks, each of said arms articulating about a pivot shaft connecting said pump cassette housing to each locking arm and one of said locking hooks located on each said locking arm to physically retain said cassette in its operative position relative to said pump mechanism, and said pump mechanism also includes a microprocessor means for monitoring the index of refraction of fluid passing through the hollow conduit arrangement and for providing control signals to said pump mechanism responsive to said monitor signals, said pump housing also includes means for storing an auxilliary battery, said battery being connected to said pump mechanism to power said pump mechanism when a main power supply is unavailable; and said cartridge structure including a rigid assymetric structure having first and second end portions connected by an intermediate raised section with a first angular structural support buttress located between said first end portion and said intermediate raised section and a second angular structural support buttress located between said second end portion and said raised section and a second angular structural support buttress located between said second end portion and said raised intermediate section, and U-shaped pump shaft openings symmetrically located in a horizontally off-center position along each wall of said cartridge structure to expose a predetermined length of said plastic tube and means for exposing a portion of the sides and base of said second connector.

* * * * *